United States Patent [19]

Budai et al.

[11] 4,285,942
[45] Aug. 25, 1981

[54] CYCLODODECANONE OXIMES

[75] Inventors: Zoltán Budai; Aranka Lay née Kónya; Tibor Mezei; Katalin Grasser; Lujza Petöcz; Enikó Kiszelly; Ibolya Kosóczky, all of Budapest, Hungary

[73] Assignee: Egyt Gyogyszervegyeszeti Gyar, Budapest, Hungary

[21] Appl. No.: 99,507

[22] Filed: Dec. 3, 1979

[30] Foreign Application Priority Data

Dec. 19, 1978 [HU] Hungary .............................. EE 2614

[51] Int. Cl.$^3$ .................... C07C 131/02; A61K 31/15; A61K 31/535
[52] U.S. Cl. .............................. 424/248.56; 564/256; 544/165; 544/398; 424/250; 424/327
[58] Field of Search ................ 260/566 AE; 424/327, 424/248.56, 250; 564/256; 544/165, 398

[56] References Cited

U.S. PATENT DOCUMENTS 1,733,462  10/1929  Kropp .......................... 260/566 AE
4,077,999  3/1978   Budai et al. .................. 260/566 AE Primary Examiner—Nicky Chan
Assistant Examiner—L. Hendriksen
Attorney, Agent, or Firm—Young & Thompson

[57] ABSTRACT

The invention relates to novel cyclododecane derivatives of the general formula

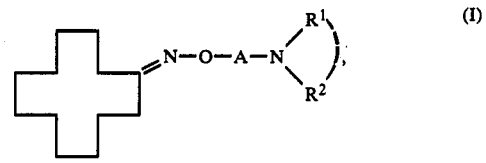

wherein $R^1$ and $R^2$ represent independently from each other a hydrogen atom, a $C_{1-6}$ alkyl group or a $C_{3-8}$ cycloalkyl group, or $R^1$ and $R^2$ form together with the nitrogen atom to which they are attached a heterocyclic ring containing 4 to 7 carbon atoms and optionally a further heteroatom selected from the group consisting of oxygen, sulphur and nitrogen, said ring may be optionally substituted by a $C_{1-3}$ alkyl or benzyl group; and A represents a $C_{2-6}$ straight or branched alkylene chain, and optically active isomers, acid addition salts and quaternary ammonium derivatives thereof. The invention relates further to an analogous process for the preparation of said compounds, to pharmaceutical compositions containing said compounds as the active ingredient and to a process for the preparation of said pharmaceutical compositions.

The cyclododecane derivatives of the invention possess valuable biological properties.

5 Claims, No Drawings

CYCLODODECANONE OXIMES

The invention relates to novel cyclododecane derivatives of the general formula

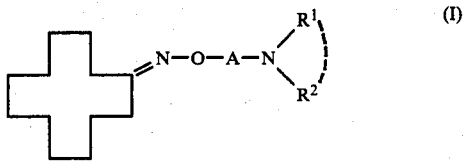

possessing valuable therapeutic effects and optically active isomers, acid addition salts and quaternary ammonium derivatives thereof, further to a process for their preparation. The invention relates also to pharmaceutical preparations containing a cyclododecane derivative of the general formula (I) as active ingredient.

In the general formula (I) $R^1$ and $R^2$ represent independently from each other a hydrogen atom, a $C_{1-6}$ alkyl group or a $C_{3-8}$ cycloalkyl group, or $R^1$ and $R^2$ form together with the nitrogen atom to which they are attached a heterocyclic ring containing 4 to 7 carbon atoms and optionally a further heteroatom, i.e. an oxygen, sulphur or nitrogen atom, and said ring may be optionally substituted by a $C_{1-3}$ alkyl or a benzyl group; and, finally, A represents a $C_{2-6}$ straight or branched alkylene chain.

The novel compounds of the general formula (I) are produced in accordance with the invention by reacting a cyclododecane derivative of the general formula

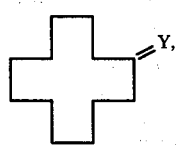

wherein Y represents an oxygen or sulphur atom or a =N—OH group with an aminoalkyl derivative of the general formula

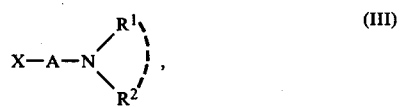

wherein X represents a halo atom or a $H_2N$—O— group, further $R^1$ and $R^2$ are as defined above, in the presence of a basic condensating agent.

The compounds of the general formula (II) are commercially available products or can be prepared in a known way (Helv. Chim. Acts 32 1949, p. 544–552).

Compounds of the general formula (III), wherein X represents a halogen atom, are similarly known and commercially available.

Compounds of the general formula (III), wherein X represents a $H_2N$—O— group, can be prepared by the method described in J. Pharm. Sci. 58, 138–140 (1969).

The reaction of the compounds of the general formula (II) and (III) is carried out in a solvent chemically inert toward the reactants, or in a mixture of such solvents. As inert solvents are, for example, the alcohols, e.g. ethanol; pyridine; triethylamine; benzene and its homologues, e.g. toluene, xylene, cumol, etc.; ethers such as tetrahydrofurane, dibutylether, etc.; dimethyl formamide or their mixtures mentioned.

In the course of the reaction of the compounds of the general formula (II) and (III) a basic condensing agent is applied. Depending on the nature of X and Y an alkali metal, suitably sodium; an alkali metal amide, suitably sodium amide; an alkali metal hydride, suitably sodium hydride; an alkali metal hydroxide, suitably sodium hydroxide; or organic bases, e.g. pyridine, picoline, triethylamine, etc. are applied as condensing agents.

The reaction is carried out in a wide temperature range, from 30° C. to 40° C. to the boiling point of the solvent used; preferably at a temperature between 70° C. and 130° C.

The compounds of the general formula (I) prepared according to the invention can be converted, if desired, into a therapeutically acceptable acid addition salt or quaternary ammonium derivative in a known way. For the production of such addition salts e.g. haloic acids, sulphuric acid, maleic acid, phosphoric acid, citric acid, tartaric acid, fumaric acid, acetic acid, propionic acid, methanesulphonic acid, etc. can be used. In order to produce quaternary ammonium compounds the compounds of the general formula (I) are allowed to react with alkyl halides or methanesulphonic acid esters suitable for quaternarisation.

The racemic mixtures of the compounds of the general formula (I) can be separated in a way known per se, e.g. by fractional crystallization of their salts with optically active acids, into the corresponding optically active isomers.

During our investigations the compounds of the general formula (I) proved to be biologically active in several tests. Of these biological effects the most significants were: the spasmolytic effect, the local anaesthetizing effect and the nicotine-lethality inhibiting effect which latter is complemented by antiarrhythmic and antiserotonine effects.

The nicotine-lethality inhibiting effect was determined on mice by the method of Stone [C. A. Stone et al.: Arch. Intern. Pharmacodynamie 117, 419/1958/], in groups consisting of ten animals each, with an oral administration. Also the toxicity values obtained by oral administration are given.

TABLE 1

| Compound (No. of chemical example) | $LD_{50}$ [mg/kg] | $ED_{50}$ [mg/kg] | Therapeutic index |
|---|---|---|---|
| 12 | 650 | 130 | 5 |
| 11 | 400 | 80 | 5 |
| 6 | 900 | 180 | 5 |
| 1 | 560 | 39 | 14.4 |
| 4 | 680 | 46 | 14.8 |
| 7 | 1100 | 68 | 16.2 |
| 2 | 780 | 28 | 27.9 |
| 5 | 800 | 10 | 80 |
| 1-cyclohexyl-1-phenyl-3-piperidino-propane-1-ol (Artane) | 365 | 40 | 9.13 |

$$\text{Therapeutic index} = \frac{LD_{50}}{ED_{50}}$$

The spasmolytic effect on smooth muscle was determined on isolated rat ileum according to the method of Brock et al. [H. Brock, J. Ceks, D. Lorenz: Arch. Exper. Path. u. Pharmacol. 215, 492/1952/] by using papaverine as the reference substance. In order to characterize the efficiency of the individual compounds their relative effect with respect to papaverine are enumerated in Table 2 below.

TABLE 2

| Compound (No. of chemical example) | Relative efficiency |
|---|---|
| 1 | 1.4 |
| 4 | 4.1 |
| 2 | 1.6 |
| 5 | 1.7 |
| 6 | 0.9 |
| 11 | 2.6 |
| 10 | 2.9 |
| Papaverine | 1.0 |

The local anaesthetizing effect was investigated on the ischiadic nerve (N. ischiadieus) of rats by the method of Truant [A. P. Truant, d'Amato cited in A. P. Truant, S. Wiedling: Acta Chirurg. Scand. 116, 351 (1958)], by using Lidocaine as the reference substance. The number of animals showing the characteristic motoric paralysis and the duration of the effect were recorded. The relative efficiency with respect to Lidocaine and the duration of the effect observed on applying a 0.25% and 0.5% concentration are presented in Table 3.

TABLE 3

| Compound (No. of chemical example) | Relative efficiency | Duration of effect [minutes] | |
|---|---|---|---|
| | | 0.25% | 0.5% |
| 1 | 0.77 | 45 | 95 |
| 4 | 0.63 | 32 | 105 |
| 2 | 0.67 | 23 | 57 |
| 5 | 0.71 | 31 | 60 |
| 6 | 0.52 | 60 | 134 |
| 11 | 1.86 | 151 | 240 |
| 10 | 2.00 | 76 | 104 |
| 12 | 1.68 | 77 | 240 |
| Lidocaine | 1.0 | 24 | 28 |

$$\text{Relative efficiency} = \frac{EC_{50} \text{ (reference compound)}}{EC_{50} \text{ (tested compound)}}$$

The compounds of the general formula (I) and therapeutically acceptable acid addition salts or quaternary ammonium derivatives thereof are converted with the use of carriers and/or auxiliary materials generally applied in the pharmaceutical production in a way known per se mainly into local anaesthetizing, antiparkinson and antiarrhythmic drugs. A single dose of a pharmaceutical composition of the invention contains generally 1 to 500 mg. of a compound of the general formula (I) or an acid addition salt or quaternary ammonium derivative thereof.

The invention is illustrated by the following Examples of non-limiting character.

EXAMPLE 1

1-(Dimethylamino-propoxyimino)cyclododecane

A solution of 19.73 g. (0.1 moles) of cyclododecanone oxime in 200 ml. of anhydrous toluene is dropwise added at 85° C. under continuous stirring to a suspension of 2.4 g. (0.1 moles) of sodium hydride in 50 ml. of anhydrous toluene, and the mixture is refluxed for 2 hours. Then 13.3 g. (0.11 moles) of 1-dimethylamino-3-chloropropane is added to the reaction mixture. After refluxing for 10 hours the mixture is cooled to room temperature, washed with 100 ml of water and extracted with a 10% solution of hydrochloric acid containing 0.11 moles of hydrochloric acid. Then the solution cooled to 0° C. is made alkaline to pH 10 with an aqueous solution of ammonium hydroxide. The base separated as an oil is extracted with dichloromethane and the solvent is removed. Yield: 21.2 g. (75.07%). Hydrogen fumarate, m.p.: 116°–118° C.

Analysis for $C_{21}H_{38}N_2O_5$: Calculated: C 63.29%, H 9.61%, N 7.03%; Found: C 63.05%, H 9.91%, N 7.07%.

EXAMPLE 2

1-(Dimethylamino-ethoxyimino)cyclododecane

Starting from 2.4 g. (0.1 moles) of sodium hydride, 19.73 g. (0.1 moles) of cyclododecanone oxime and 11.8 g. (0.11 moles) of 1-dimethylamino-2-chloroethane the title compound is prepared as in Example 1. Yield: 19.5 g. (72.65%). Hydrogen fumarate, m.p.: 108°–110° C.

Analysis for $C_{20}H_{34}N_2O_5$: Calculated: C 62.41%, H 9.44%, N 7.29%; Found: C 62.70%, H 9.39%; N 7.50%.

EXAMPLE 3

1-(Diethylamino-ethoxyimino)cyclododecane

The sodium salt is formed in the usual way from 2.4 g. (0.1 moles) of sodium hydride and 19.73 g. (0.1 moles) of cyclododecanone oxime in a toluenic solution and then allowed to react with 14.9 g. (0.11 moles) of 1-diethylamino-2-chloroethane. Otherwise the operations are carried out in accordance with Example 1. Yield: 20 g. (67.56%); b.p. 172°–176° C./0.8 torr. Hydrogen fumarate, m.p.: 112°–114° C.

Analysis for $C_{22}H_{40}N_2O_5$: Calculated: C 64.02%, H 9.76%, N 6.82%; Found: C 64.15%, H 9.82%, N 6.80%.

EXAMPLE 4

D,L-1-(3'-Dimethylamino-2'-methylpropoxyimino)cyclododecane

Starting from 2.4 g. (0.1 moles) of sodium hydride, 19.73 g. (0.1 moles) of cyclododecanone oxime and 16.5 g. (0.12 moles) of 1-dimethylamino-3-chloro-2-methylpropane the title compound is prepared as in Example 1. Yield: 21.48 g. (72.56%); b.p.: 158°–160° C./0.8 torr. Hydrogen fumarate, m.p.: 178°–179° C.

Analysis for $C_{22}H_{40}N_2O_5$: Calculated: C 64.05%, H 9.77%, N 6.79%; Found: C 63.78%, H 9.80%, N 6.89%.

EXAMPLE 5

1-(Diisopropylamino-ethoxyimino)cyclododecane

Starting from 2.4 g. (0.1 moles) of sodium hydride, 19.73 g. (0.1 moles) of cyclododecanone oxime and 17.95 g. (0.11 moles) of 1-diisopropylamino-2-chloroethane the title compound is prepared as in Example 1. Yield: 22.1 g. (68.20%); b.p.: 164°–166° C./0.6 torr. Hydrogen fumarate, m.p.: 120°–121° C.

Analysis for $C_{22}H_{44}N_2O_5$: Calculated: C 65.42%, H 10.07%, N 6.35%; Found: C 65.22%, H 10.20%, N 6.32%.

EXAMPLE 6

1-(N-Benzylpiperazinyl-propoxyimino)cyclododecane

A solution of 19.73 g. (0.1 moles) of cyclododecanone in 200 ml. of anhydrous toluene is dropwise added at 85° C. under stirring to a suspension of 2.4 g. (0.1 moles) of sodium hydride in 50 ml. of anhydrous toluene. The reaction mixture is boiled for two hours, then a solution of 27.8 g. (0.11 moles) of 1-(N-benzylpiperazinyl)-3-chloropropane in 50 ml. of anhydrous toluene is added. The reaction becomes complete after several hours of reflux. Then the reaction mixture is cooled below 30° C., shaken with a solution of 35 g. of tartaric acid in 100 ml. of water and the acidic aqueous solution, after its separation, made alkaline to pH 10 with a concentrated aqueous solution of ammonium hydroxide, then extracted with dichloroethane and the solvent removed. Yield: 31.1 g. (75.3%).

Dihydrogen fumarate, m.p.: 213°–215° C.

Analysis for $C_{34}H_{51}N_3O_9$: Calculated: C 63.14%, H 8.10%, N 6.49%; Found: C 63.05%, H 8.15%, N 6.47%.

Dihydrogen maleate, m.p.: 201°–204° C.

Analysis for $C_{34}H_{51}N_3O_9$: Calculated: C 63.14%, H 8.10%, N 6.49%; Found: C 63.25%, H 8.20%, N 6.48%.

Dihydrochloride, m.p.: 220°–221° C.

Analysis for $C_{26}H_{45}N_3Cl_2O$: Calculated: C 64.17%, H 9.32%, N 8.63%, Cl 14.57%; Found: C 64.02%, H 9.50%, N 8.58%, Cl 14.32%.

Iodomethylate, m.p.: 157°–161° C.

Analysis for $C_{27}H_{46}N_3IO$: Calculated: C 58.36%, H 8.34%, N 2.87%, I 22.84%; Found: C 58.28%, H 8.42%, N 2.85%, I 22.68%.

EXAMPLE 7

1-(N-methylpiperazinyl-propoxyimino)cyclododecane

Starting from 2.4 g. (0.1 moles) of sodium hydride, 19.73 g. (0.1 moles) of cyclododecanone oxime and 19.5 g. (0.11 moles) of 1-chloro-3-(N-methylpiperazinyl)propane the title compound is prepared as in Example 6. Yield: 20.9 g. (62.0%). Dihydrogen fumarate, m.p.: 210°–213° C.

Analysis for $C_{28}H_{47}N_3O_9$: Calculated: C 58.89%, H 8.31%, N 7.37%; Found: C 58.72%, H 8.50%, N 7.39%.

EXAMPLE 8

1-(3'-Morpholino-propoxyimino)cyclododecane

The sodium salt is formed from 2.4 g. (0.1 moles) of sodium hydride and 19.73 g. (0.1 moles) of cyclododecanone oxime in a toluenic medium, then it is reacted with 18.0 g. (0.11 moles) of 1-chloro-3-morpholinopropane. Thereafter one proceeds as in Example 1. Yield: 22.22 g. (68.5%). Hydrogen fumarate, m.p.: 118°–120° C.

Analysis for $C_{23}H_{40}N_2O_6$: Calculated: C 62.70%, H 9.15%, N 6.35%; Found: C 62.45%, H 9.07%, N 6.43%.

EXAMPLE 9

1-(N-Cyclohexyl-N-methylamino-propoxyimino)cyclododecane

The sodium salt is formed from 2.4 g. (0.1 moles) of sodium hydride and 19.73 g. (0.1 moles) of cyclododecanone oxime in a toluenic medium, then it is reacted with 19.96 g. (0.105 moles) of 1-(N-cyclohexyl-N-methylamino)-3-chloropropane. Thereafter one proceeds as in Example 6. Yield: 22.9 g. (65.7%). Hydrogen fumarate, m.p.: 130°–135° C.

Analysis for $C_{26}H_{46}N_2O_5$: Calculated: C 66.92%, H 9.93%, N 6.00%; Found: C 66.67%, H 9.98%, N 6.03%.

EXAMPLE 10

1-(Diethylamino-propoxyimino)cyclododecane

The sodium salt of cyclododecanone oxime is prepared in a xylenic solution from 19.7 g. (0.1 moles) of cyclododecanone oxime and 3.9 g. (0.1 moles) of sodium amide, then it is reacted at the boiling point of the reaction mixture with 16.46 g. (0.11 moles) of 1-diethylamino-3-chloropropane. Thereafter one proceeds as in Example 1. Yield: 24.59 g. (79.2%). Hydrogen fumarate, m.p.: 96°–98° C.

Analysis for $C_{23}H_{42}N_2O_5$: Calculated: C 64.76%, H 9.90%, N 6.57%; Found: C 64.65%, H 9.88%, N 6.53%.

EXAMPLE 11

1-(3'-Diethylamino-2'-methyl-propoxyimino)cyclododecane 19.7 g. (0.1 moles) of cyclododecanone oxime is reacted at first with 2.4 g. (0.1 moles) of sodium hydride, then with 18 g. (0.11 moles) of 1-dimethylamino-3-chloro-2-methylpropane in a solution formed with xylene. Thereafter one proceeds as in Example 1. Yield: 23.7 g. (73.0%). Hydrogen fumarate, m.p.: 177°–179° C.

Analysis: for $C_{24}H_{44}N_2O_5$: Calculated: C 65.42%, H 10.06%, N 6.3%; Found: C 65.50%, H 10.02%, N 6.31%.

EXAMPLE 12

1-(Diisopropylamino-propoxyimino)cyclododecane

Starting from 19.7 g. (0.1 moles) of cyclododecanone oxime, 2.4 g. (0.1 moles) of sodium hydride and 19.55 g. (0.11 moles) of 1-diisopropylamino-3-chloropropane the title product is prepared as in Example 1. Yield: 24.2 g. (71.6%). Hydrogen fumarate, m.p.: 119°–121° C.

Analysis for $C_{25}H_{46}N_2O_5$: Calculated: C 66.05%, H 10.2%, N 6.2%; Found: C 66.15%, H 10.1%, N 6.3%.

EXAMPLE 13

1-(Dimethylamino-ethoxyimino)cyclododecane

A mixture of 19.84 g. (0.1 moles) of cyclododecathione and 17.7 g. (0.103 moles) of dimethylaminoethoxyamine dihydrochloride are boiled for several hours in a mixture of 150 ml of anhydrous ethanol and 74 ml of anhydrous pyridine, then the solvents are removed in vacuum. After making the residue alkaline to pH 10 with a 40% aqueous solution of sodium hydroxide the title compound is extracted with dichloroethane and finally the solvent is removed. Yield: 20.4 g. (76%). Hydrogen fumarate, m.p.: 108°–110° C.

EXAMPLE 14

1-(Diethylamino-ethoxyimino)cyclododecane

Starting from 18.23 g. (0.1 moles) of cyclododecanone and 22.56 g. (0.11 moles) of diethylamino-ethoxyamine dihydrochloride the title compound is prepared as in Example 13. Yield: 22 g. (74.3%). Hydrogen fumarate, m.p.: 112°–114° C.

EXAMPLE 15

1-(Diisopropylamino-ethoxyimino(cyclododecane

Starting from 18.23 g. (0.1 moles) of cyclododecanone and 23.9 g. (0.103 moles) of diisopropylamino-ethoxyamine dihydrochloride the title compound is prepared as in Example 13. Yield: 21 g. (64.8%). Hydrogen fumarate, m.p.: 120°–121° C.

EXAMPLE 16

1-(Dimethylamino-propoxyimino)cyclododecane

Starting from 18.23 g. (0.1 moles) of cyclododecanone and 21.0 g. (0.11 moles) of dimethylaminopropoxyamine dihydrochloride the title compound is prepared as in Example 13. Yield: 20.9 g. (74%). Hydrogen fumarate, m.p.: 117°–118° C.

EXAMPLE 17

1-(Diethylamino-propoxyimino)cyclododecane

Starting from 18.23 g. (0.1 moles) of cyclododecanone and 24.1 g. (0.1 moles) of diethylaminopropoxyamine dihydrochloride, the title compound is prepared as in Example 13. Yield: 25.7 g. (82.77%). Hydrogen fumarate, m.p.: 97°–98° C.

EXAMPLE 18

1-(Diisopropylamino-propoxyimino)cyclododecane

Starting from 18.23 g. (0.1 moles) of cyclododecanone and 30.16 g. (0.12 moles) of diisopropylaminopropoxyamine dihydrochloride the title compound is prepared as in Example 13. Yield: 24.2 g. (71.6%). Hydrogen fumarate, m.p.: 119°–121° C.

EXAMPLE 19

1-(Morpholino-propoxyimino)cyclododecane

Starting from 18.23 g. (0.1 moles) of cyclododecanone and 25.64 g. (0.11 moles) of morpholinopropoxyamine dihydrochloride the title compound is prepared as in Example 13. Yield: 28.4 g. (87%). Hydrogen fumarate, m.p.: 118°–120° C.

EXAMPLE 20

1-(N-Methylpiperazinyl-propoxyimino)cyclododecane

Starting from 18.23 g. (0.1 moles of cyclododecanone and 31.1 g. (0.11 moles) of N-methylpiperazinylpropoxyamine trihydrochloride the title compound is prepared as in Example 13. Yield: 18 g. (53.4%). Dihydrogen fumarate, m.p.: 210°–213° C.

EXAMPLE 21

1-(N-Benzylpiperazinyl-propoxyimino)cyclododecane

Starting from 18.23 g. (0.1 moles) of cyclododecanone and 39.5 g. (0.11 moles) of N-benzylpiperazinylpropoxyamine trihydrochloride the title compound is prepared as in Example 13. Yield: 27.5 g. (66.6%). Dihydrogen maleate, m.p.: 203°–204° C.

EXAMPLE 22

1-(N-Cyclohexyl-N-methylamino-propoxyimino)cyclododecane

Starting from 18.23 g. (0.1 moles) of cyclododecanone and 28.5 g. (0.11 moles) of N-cyclohexyl-N-methylaminopropoxyamine dihydrochloride the title compound is prepared as in Example 13. Yield: 20.45 g. (58.67%). Hydrogen fumarate, m.p.: 133°–135° C.

EXAMPLE 23 d,l-1-(3'-Dimethylamino-2'-methylpropoxyimino)cyclododecane

Starting from 18.23 g. (0.1 moles) of cyclododecanone and 30.76 g. (0.16 moles) of d,l-dimethylamino-2-methylpropoxyamino dihydrochloride the title compound is prepared as in Example 13. Yield: 20 g. (67.56%). Hydrogen fumarate, m.p.: 125°–128° C.

EXAMPLE 24 d,l-(3'-Diethylamino-2'-methylpropoxyimino)cyclododecane

Starting from 18.23 g. (0.1 moles) of cyclododecanone and 30.3 g. (0.13 moles) of 1-diethylamino-2-methylpropoxyamine dihydrochloride the title compound is prepared as in Example 13. Yield: 24 g. (73.9%). Hydrogen fumarate, m.p.: 178°–179° C.

EXAMPLE 25

Tablets containing 25 mg. of 1-(dimethylaminopropoxyimino)cyclododecane hydrogen fumarate are prepared.

The composition of a tablet is as follows:

| | |
|---|---|
| Active substance | 25.0 mg. |
| Maize starch | 97.0 mg. |
| Polyvinyl pyrrolidone | 175.0 mg. |
| Magnesium stearate | 3.0 mg. |
| | 300.0 mg. |

After moistening with a 10–15% aqueous solution of polyvinyl pyrrolidone, a mixture of the active substance and the maize starch is granulated and subsequently dried at 40°–45° C. After repeated drying the granulate is mixed with the magnesium stearate and pressed into tablets. The weight of a tablet is equal to 300 mg.

EXAMPLE 26

Dragées containing 25 mg. of 1-(diethylamino-ethoxyimino)cyclododecane hydrogen fumarate are prepared.

The composition of a dragée kernel is as follows:

| | |
|---|---|
| Active substance | 25.0 mg |
| Maize starch | 245.0 mg |
| Gelatine | 8.0 mg. |
| Talc | 18.0 mg. |
| Magnesium stearate | 4.0 mg. |
| | 300.0 mg. |

A mixture of the active substance and the maize starch is moistened with a 10% aqueous gelatine solution, then granulated by passing through a sieve and dried at 40°–45° C. The dry granulate is repeatedly rubbed through a sieve, homogenized with the talc and the magnesium stearate, finally compressed to dragée kernels of 300 mg. each.

EXAMPLE 27

Dragées containing 50 mg. of 1-(diisopropylaminopropoxyimino)cyclododecane hydrogen fumarate are prepared.

The composition of a dragée kernel is as follows:

| | |
|---|---|
| Active substance | 50.0 mg. |
| Lactose | 97.0 mg. |
| Polyvinyl pyrrolidone | 2.0 mg. |
| Magnesium stearate | 1.0 mg. |
| | 150.0 mg. |

The granulate is prepared as in the foregoing Example. The dragée kernels are coated in a manner known per se, by a layer consisting of sugar and talc. The finished dragée is stained with a non-toxic food pigment to the desired colour and polished with beewax.

EXAMPLE 28

Gelatine capsules containing 25 mg. of 1-(diethylaminoethoxyimino)cyclododecane hydrogen fumarate are prepared.

The composition of a gelatine capsule is as follows:

| Active substance | 25.0 mg. |
| --- | --- |
| Maize starch | 265.0 mg. |
| Aerosil (silicon dioxide) | 6.0 mg. |
| Magnesium stearate | 4.0 mg. |
| | 300.0 mg. |

The components are homogenized and then filled into gelatine capsules of the adequate size.

EXAMPLE 29

An injectable solution containing 25 mg. of 1-(dimethylaminopropoxyimino)-cyclododecane hydrogen fumarate is prepared.

An ampoule contains 25.0 mg. of the active substance in 5 ml. of twice distilled water.

What we claim is:

1. A cyclododecane derivative of the general formula

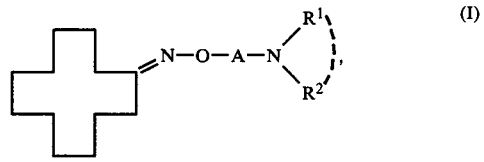

wherein $R^1$ and $R^2$ represent independently from each other a hydrogen atom, a $C_{1-6}$ alkyl group or a $C_{3-8}$ cycloalkyl group, or $R^1$ and $R^2$ form together with the nitrogen atom to which they are attached a morpholine or piperazine, and said ring may be optionally substituted by a $C_{1-3}$ alkyl or a benzyl group; and A represents a $C_{2-6}$ straight or branched alkylene chain, or an optically active isomer or pharmaceutically acceptable acid addition salt thereof.

2. 1-/Diethylamino-propoxyimino/cyclododecane.

3. 1-/3'-Diethylamino-2'-methyl-propoxyimino/cyclododecane.

4. 1-/Diisopropylamino-propoxyimino/cyclododecane.

5. A pharmaceutical composition having spasmolytic, local anesthetizing and nicotine-lethality inhibiting effect, containing a pharmaceutically effective amount of a cyclododecane derivative as claimed in claim 1 as the active agent, and a pharmaceutically acceptable excipient therefor.

* * * * *